United States Patent [19]

Schwartz

[11] Patent Number: 5,859,057
[45] Date of Patent: Jan. 12, 1999

[54] COCKROACH REPELLENT

[76] Inventor: Alan M. Schwartz, 49 Fabriano, Irvine, Calif. 92720-2525

[21] Appl. No.: 534,844

[22] Filed: Sep. 27, 1995

[51] Int. Cl.[6] .......................... A01N 37/06; A01N 25/00; A01N 25/22; A01N 25/34

[52] U.S. Cl. .......................... 514/560; 514/558; 514/919; 514/970; 514/972; 424/400; 424/403; 424/405; 424/408; 424/409; 424/410; 424/411; 424/412; 424/413; 424/414; 424/417; 424/484; 424/DIG. 10

[58] Field of Search ...................... 514/557, 558, 514/919, 560, 970, 972; 424/400, 402, 403, 405, 408, 409, 411–415, 417–421, 484, DIG. 10

[56] References Cited

U.S. PATENT DOCUMENTS

| | | | |
|---|---|---|---|
| 4,804,683 | 2/1989 | Steltenkamp | 514/629 |
| 4,849,279 | 7/1989 | Toyama et al. | 428/224 |
| 4,923,607 | 5/1990 | Ninomiya et al. | 210/490 |
| 5,030,660 | 7/1991 | Norris et al. | 514/762 |
| 5,102,662 | 4/1992 | Gallagher | 424/409 |

OTHER PUBLICATIONS

Chemical Abstracts 85: 15364, 1976.
Rollo et al., "Fatty Acid Necromones for Cockroaches" Naturwissenschaften, vol. 81 (9), 1994, pp. 409–410.
Chemical Abstracts 77: 86698h (1972).

*Primary Examiner*—John Pak
*Attorney, Agent, or Firm*—Peter Jon Gluck; Patent Law Firm; Francis X. Lojacono

[57] ABSTRACT

A cockroach repellent comprising a non-toxic, non-noxious, non-corrosive compound that is substantially odorless to humans and organisms except to cockroaches, wherein the present invention provides an environmentally safe cockroach repellent that consists of various compositions of matter that includes a mixture of selective amounts of linoleic acid together with a suitable antioxidant preservative which creates a non-noxious vaporous pheromic substance that is repellent to cockroach presence and prevents subsequent infestation in a given area, the compound being synergistic in prolonging over time the desirable action of the invention, and whose vapors do not form a flammable mixture with air.

28 Claims, No Drawings

COCKROACH REPELLENT

BACKGROUND OF THE INVENTION

1. Field of the Invention

This invention relates generally to an insect repellent and more particularly to a non-toxic, non-noxious, non-corrosive cockroach repellent that is substantially odorless to humans and organisms other than cockroaches and is adapted to be impregnated in various carriers such as any suitable porous receiving pad or the like.

2. Description of Prior Art

Sundry formulations and mechanisms have been synthesized and employed to discourage or prevent cockroach infiltration and infestation within otherwise attractive areas and volumes. No real world application of any reported invention is known to be operationally safe and effective. It has been well established that electric and/or electronic equipment is attractive to cockroach infestation by virtue of its warmth and secluded areas and volumes; suffers damage and destruction therefrom; causing owners to suffer financial loss resulting from loss of operating time, incurred liabilities, repair costs, and replacement costs. Accordingly, what is needed is a cockroach repellent which would deny cockroaches access to these sensitive areas by activating a natural mechanism of dissuasion, without deleteriously affecting other organisms or the equipment, that would be humane and provide an effective advantage for humans.

Cockroach infestation has been an objectionable occurrence visited against habitation, storage, and equipment throughout history. Attempted control by folk remedies has not been effective. Attempted control by poison and other lethal technological means has not been effective, nor is it without harmful effects upon people, other organisms, the biosphere as a whole; and the objects, areas, and volumes for which amelioration is sought.

Deleterious effects of cockroach presence and infestation are commonly found in warm places such as sensitive interior compartments relating to components of electric and electronic devices. Such examples comprise scales, cash registers, optical scanners, and computers that often suffer damage and incapacitation from cockroach presence and infestation. This creates and causes a precipitating economic loss for their owners through loss of operation, repair costs, and replacement costs. Such devices as mentioned above are especially attractive to cockroach intrusion by virtue of their warmth during operation and the seclusion of their internal areas and volumes. The prior art fails to teach a composition of matter capable of emitting a vaporous pheromonic substance repellent to cockroach presence and subsequent infestation, thus employing recognition and warning chemistry intrinsic to natural cockroach behavior.

Analysis of the prior art fails to educate, indicate, identify, or specify a safe and effective interiorly or topically emplaced modality or apparatus for the safe and effective prevention of cockroach infestation of such devices, and further fails to teach a composition of matter capable of emitting an insect behavior-modifying pheromonic substance that is safe to release within enclosed compartments and more particularly compartments having components of electric and electronic devices.

In U.S. Pat. No. 4,876,090, issued to Richard Weisler, there is disclosed a systemic insect repellent composition which comprises two essential ingredients: Vitamin B and allyl sulfide (garlic oil) dissolved in a soybean oil base.

OBJECTS AND ADVANTAGES OF THE INVENTION

It is an important object of the present invention to provide a safe, rapidly effective cockroach repellent having a sustained action, and powerful cockroach infestation disincentive agent that defines a non-noxious, vaporous, pheromonic substance that is a specific repellent to cockroaches, whereby the benign agent would serve to preserve from the deleterious effects of cockroach presence and infestation such areas as the sensitive interior components of electric and electronic devices such as scales, cash registers, optical scanners, computers and other warmed and secluded areas that are readily adapted for such roach infestation. It is further suitable for excluding cockroach presence and infestation even in sensitive areas such as medical equipment and facilities, food storage, and food preparation areas.

Another object of the invention is to provide a safe cockroach repellent which comprises various chemical substances that are specifically designed to emit a compound that influences cockroaches to travel away from such treated areas without causing any effect upon other organisms.

It is still another object of the present invention to provide a cockroach repellent consisting of a non-toxic, non-noxious, non-corrosive compound that is substantially odorless to humans and organisms other than cockroaches.

Still another important object of the present invention is to provide an environmentally safe cockroach repellent that consists of various compositions of matter that includes a mixture of selective amounts of linoleic acid together with a suitable antioxidant preservation composition as will be hereinafter described.

A further object of the invention is to provide an environmentally safe cockroach repellent that can be selectively stored in dimensionally small absorbent material that is formed from a matrix capable of retaining the compounded active fluid and allowing a rate of escape of a sufficiency of its vapors, or to be added as necessary such excipients as to render the invention suitable for emplacement and dispensing as a non-imobilized fluid.

A still further object of the present invention is to provide a repellent of this character that is capable of being stored in a sealed container such as a barrier package or envelope for containing the embodied invention for handling, transporting and storage thereof prior to its placement and use which protects and preserves the repellent material against an exogenous environment that might affect the embodied repellent.

It may thus be seen that the objects of the present invention set forth herein, as well as those made apparent from the foregoing description, are efficiently attained. While the preferred embodiments of the invention have been set forth for purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

DETAILED DESCRIPTION OF THE PREFERRED EMBODIMENT

This invention discloses a cockroach repellent consisting of a non-toxic, non-noxious, non-corrosive compound, that is substantially odorless to humans and organisms comprising a spontaneously deactivating, biodegradable composition of matter which possesses a sustained temporal activity and whose vapors do not form a flammable mixture with air. Its embodiment is particularly useful in emplacements and devices for substantially repelling the undesired visitation of areas and volumes by cockroaches.

The present cockroach repellent is suitable for excluding cockroach presence and infestation even in sensitive areas such as medical equipment and facilities, food storage and preparation areas, and sophisticated electronic equipment.

The active substance semiotic pheromone of the subject invention, naturally signaling to spatially proximate cockroaches that the treated area is unattractive and not desirable for cockroach presence, is linoleic acid. It may be substantially pure, or a majority component of a less pure mixture derived from natural or synthetic sources. Linoleic acid is subject to chemical reaction with oxygen and air pollution, rendering it inactive. The inactivation is exacerbated and speeded by the presence of light. The chemical reaction products of the degradation promote further and more rapid reaction of remaining linoleic acid. Physical changes due to the degradation, the thickening and eventual gelling of the liquid linoleic acid, lessen both its vapor pressure and its rate of evaporation, deleteriously lessening its cockroach-repellent action and deleteriously limiting the action to smaller areas and volumes.

Incorporated within the invention is one or more antioxidant agents which serve to substantially prolong the desirable action of the linoleic acid. The antioxidant agents protect its chemical and physical integrity against reaction with oxygen and air pollution alone or in the presence of light. There exists an abundance of suitable antioxidants consisting of commercial and specialty chemicals and their combinations, mixtures and proprietary compositions that are well known to those educated in the art. Many of these antioxidant agents can be employed to advantageously prolong the desirable cockroach-repellent activities of the invention when incorporated within linoleic acid. One particular antioxidant agent, NDGA, possesses a particularly effective and safe activity, and is the preferred embodiment within the invention to prolong and intensify its action over time. This combination is thus synergistic, the sum of the components exerting an effect greater than a linear combination of the isolated effects of the single components taken in isolation.

Linoleic acid plus antioxidant is an oily liquid difficult to dispense in the minuscule quantities necessary for advantageous cockroach repellency, and possibly destructive of susceptible electronic and other components; paints, varnishes, and other protective and decorative technique; adherent or adhesive surface embellishments; contact areas between moving parts; and other circumstances wherein an oily liquid is undesirable. A suitable quantity of active agent may therefore be specifically contained within an absorptive or adsorptive entity consisting of a plurality of macroscopic or microscopic interstices constituting a matrix capable of retaining the compounded active fluid and allowing a rate of escape of a sufficiency of its vapors to exert its cockroach-repellent effect through the desired area or volume. Such an entity of small dimension and volume would comprise a woven or non-woven fabric pad of natural, synthetic, or recycled fiber either homogeneous in composition or constituting a mixture of fiber types; a natural or synthetic sponge; a suitably porous ceramic pellet or plate; a stable polymer or other foam retaining communicating interstices; a colloidal or other gel possessing microscopic interstices capable of imbibing and dispensing the active composition; and a plasticized matrix which blooms or otherwise dispenses the active volatile component over time and in sufficient effective quantities.

Linoleic acid even with antioxidant protection is unstable toward the presence of oxygen, air pollution, and light. A containing entity may lose its activity through this degradation mechanism, and even by common contact with objects upon which contained fluid may be transferred. The beneficial cockroach-repellent effects of the invention would deleteriously effect normal cockroach activity were it not repressed prior to emplacement prior to desired point of action. The embodied roach compound must therefore itself be contained within a sealed container such a barrier package or envelope that is impermeable to oxygen, air pollution, and light. Such a barrier package or envelope may be fabricated from the following materials and arrangements thereof:

1) inner layer or layers physically and chemically inert to the effects of the various components of the cockroach repellent singly and in combination. Thus, an inner layer might comprise one or more foils, films, or deposited continuous layers of polyolefin polymers such as polyethylene or polypropylene, or any other natural or synthetic materials, such as condensation or addition polymers of suitable resistance, dimensionality, and physical survivability.

2) a middle layer or layers impermeable to oxygen, air pollution, and light so as to isolate the cockroach repellent compound from the deleterious and degradative effects of exogenous contamination, wherein the inner layer or layers might consist of a metal film, foil, or deposition such as aluminum or a thin and flexible deposit of silicate or other inorganic substance. It is also contemplated that films, foils, or deposits of natural or synthetic barrier polymers such as nylon or butyl rubber may also be employed to isolate the novel compound.

3) outer layer or layers suitable for imprinting and sanitary handling.

4) the whole serving to contain and protect the contents comprising the active Ingredients of the invention; to contain and isolate the active compound from influencing and exerting its cockroach repellent effect upon the exogenous environment; and to serve as an a facile dispenser for the active invention and its embodiment within its absorptive or adsorptive entity prior to emplacement within the environment to be rendered.

However, it should be further noted that in cases where the presence of an oily fluid is not objectionable, suitable excipients, if any, may be added to allow dispensing and emplacement of advantageous net quantities of the compounded roach-repellent material as a non-imobilized fluid. Accordingly, various types of applicators may be employed such as droppers, squirters, aerosols neat or in an air or gas stream, continuous or pulsed pressurized dispersion through an orifice, or direct bulk distribution upon a surface through the intermediacy of a wipe, swab, brush or other suitable applicators. The containment vessel which holds the fluid emplacement embodiment of the invention must also exhibit the barrier properties of the barrier container, pouch or envelope, as noted above. This invention despite it efficacy for repelling cockroaches is innocuous and safe toward humans when used as recommended. It is without deleterious effect upon materials of construction, storage containers, applicators, or other inanimate surfaces or materials with which it may properly be brought into contact.

The present invention is a composition of matter created from active materials in particular contingent proportions by weight with maximal synergistic potency that is obtained by combination of linoleic acid consisting of a substantially pure (Z,Z)-9,12-octadienoic acid having at least 10% by weight of liquid volatiles, bun preferentially 90% to 99.9% serving as the natural semiotic pheromonic substance that is repellent to cockroach presence and subsequent infestation in a given area; and an antioxidant 4,4'-(2,3-dimethyl-1,4- butanediyl)bis[1,2-benzenediol] hereinafter referred to as nordihydroguaiaretic acid (NDGA), in amounts of at least 0.001% by weight of the total composition, but preferably between 0.01% and solution saturation within the linoleic acid, although other suitable antioxidants and combinations of antioxidants employed in the same amounts can be chosen from single representatives or mixtures of non-alkaline lipophilic phenolic antioxidants, notably low molecular weight agents such as the following: 2,6-di-tert-butyl-4-methylphenol (BHT), phytic acid, gallates and gallate derivatives, existing commercial mixtures such as Tenox® antioxidants (Eastman Chemical Co.), natural or synthetic tocopherols; higher molecular weight or oligomeric or polymeric non-alkaline lipophilic phenolic antioxidants such as Irganox® 1010 (Ciba-Geigy Corn.) or Trolox® (Hoffman-LaRoche) 6-hydroxy-2,5,7,8-tetramethylchroman-2-carboxylic acid or other non-alkaline lipophilic antioxidants such as ascorbic acid palmitate, these and related substances generally known to those skilled in the art.

The compounded fluid is preferably provided in the amount of 30 microliters, but acceptably in the amounts of one microliter to 500 microliters is to be preferentially absorbed in a non-woven pad of recycled polyester fiber felt. The pad plus its aliquot of active agent is to be packaged in a three-layer sealed barrier container that is defined by a pouch or envelope consisting of a polyester film or paper outer layer upon which may be printed suitable indicia to provide information and identifying marks. The barrier container comprises a middle layer of continuous aluminum foil, and an inner layer of polyethylene film sealed by a suitable sealing means that provides an adherent and sealed package by the application of adhesive agents, heat, or other unifying modalities. The suitable container shall further include a notch or other construction that defines a means to allow it to be readily opened at the point of application without use of tools or an objectionable preponderance of destructive physical force.

Accordingly, the present invention encompasses a cockroach repellent and process for safely storing the repellent in a package or container so as not to destroy the integrity of the repellent before it is subjected to use. The preferred composition of the cockroach repellent comprises linoleic acid and an antioxidant preservative agent mixed in the following relative quantities:

EXAMPLE I

| linoleic acid | 10%–99.9% by weight |
|---|---|
| antioxidant preservative agent | 0.001%–0.1% by weight |

The amount of linoleic acid comprises a natural or synthetically derived substantially pure (Z,Z)-9,12- octadienoic acid having at least 10% by weight of liquid volatiles, but preferentially 90% to 99.9% by weight serving as the natural semiotic pheromonic substance repellent to cockroach presence and subsequent infestation. The suitable antioxidant preservation of matter was preferentially chosen from single representatives of non-alkaline lipophilic phenolic antioxidants, consisting of 4,4'-(2,3-dimethyl-1,4-butanediyl)bis[1,2-benzenediol], generally referred to as nor-dihydroguaiaretic acid (NDGA), which comprises from 0.001%–0.1% by weight.

An example of another mixture of the above ingredients which has been found to form a stable compound for repelling cockroaches is as follows:

EXAMPLE II

| Linoleic acid, a natural semiotic pheromonic substance | 90% |
|---|---|
| Nordihydroguaiaretic acid (NDGA) | .01% |

EXAMPLE III

To produce 500 grams of Industrene 225 (56% by weight Linoleic Acid) is added 0.01% by weight NDGA, followed by vigorous mixing until solution is achieved, thereby producing 500.05 grams of the active ingredient of the invention.

After the mixture is formed it is then transferred to a carrier means such as a suitable container that is in turn preserved within a sealed pouch or envelope as heretofore described.

The foregoing should only be considered as illustrative of the principles of the invention. Further, since numerous modifications and changes may readily occur to those skilled in the art, it is not desired to limit the invention to the exact compositions of components and materials as described herein, and accordingly, all suitable modifications and equivalents may be resorted to, falling within the scope of the claimed invention.

What I claim is:

1. A sustained action non-toxic vaporous pheromonic cockroach repellent that reduces infestation of cockroaches in a given area or compartment comprising a carrier means that is selectively impregnated with an effective amount of a solution consisting essentially of linoleic acid in amounts between 10%–99.9% by weight and an antioxidant preservative agent in amounts from 0.001%–0.1% by weight; wherein the selectively impregnated carrier means is stored in a sealed container prior to being employed.

2. The sustained action non-toxic vaporous pheromonic cockroach repellent as recited in claim 1, wherein said antioxidant preservative agent consists of nordihydroguaiaretic acid (NDGA).

3. The sustained action non-toxic vaporous pheromonic cockroach repellent as recited in claim 1, wherein said linoleic acid consists of (Z,Z)-9, 12-octadienoic acid.

4. The sustained action non-toxic vaporous pheromonic cockroach repellent as recited in claim 3, wherein said antioxidant preservative agent consists of 4,4'-(2,3-dimethyl-1,4-butanediyl)bis[1,2-benzenediol].

5. The sustained action non-toxic vaporous pheromonic cockroach repellent as recited in claim 3, wherein said antioxidant preservative agent is selected from the group consisting of 2,6-di-tert-butyl-4-methylphenol (BHT),phytic acid, gallates, gallate derivative, 6-hydroxy-2,5,7,8-tetramethylchroman-2-carboxylic acid and natural or synthetic tocopherols.

6. The sustained action non-toxic vaporous pheromonic cockroach repellent as recited in claim 3, wherein said antioxidant preservative agent is selected from the group consisting of oligomeric and polymeric non-alkaline lipophilic antioxidants.

7. The sustained action non-toxic vaporous pheromonic cockroach repellent as recited in claim 1, wherein said carrier means comprises an absorbent pad being a matrix for retaining the selectively impregnated solution to allow a rate of escape of a sufficiency of the vapors from said solution to exert the cockroach repellent effectively throughout the desired area in which said absorbent pad is located.

8. The sustained action non-toxic vaporous pheromonic cockroach repellent as recited in claim 7, wherein said matrix of said pad composes a fabric material.

9. The sustained action non-toxic vaporous pheromonic cockroach repellent as recited in claim 7, wherein said matrix of said pad comprises a permeable plastic material.

10. The sustained action non-toxic vaporous pheromonic cockroach repellent as recited in claim 7, wherein said matrix of said pad comprises a porous ceramic material.

11. The sustained action non-toxic vaporous pheromonic cockroach repellent as recited in claim 1, wherein said sealed container comprises a barrier package that is impermeable to oxygen, air pollution, and light.

12. The sustained action non-toxic vaporous pheromonic cockroach repellent as recited in claim 11, wherein said barrier package is formed from a group of selective materials consisting of metal foils, films and continuous layers of condensation polymers.

13. The sustained action non-toxic vaporous pheromonic cockroach repellent as recited in claim 11, wherein said barrier package is formed from a group of selective materials consisting of metal foils, films and continuous layers of addition polymers.

14. A method of treating and establishing a cockroach free zone within given perimeters of a structure comprising the steps of:
providing a solution consisting essentially of linoleic acrid and an antioxidant preservative agent in selective amounts to create an effective non-noxious vaporous pheromonic substance that specifically repels cockroaches;
selectively impregnating an effective amount of said solution on a carrier means; and
placing said carrier means with given perimeters of a structure, whereby the vapors from said solution permeates the surrounding area within the structure, thereby reducing infestation of cockroaches therein.

15. The method of claim 14, wherein the effective amount of said solution consists of at least 10% to 99.9% by weight of said linoleic acid and of at least 0001% to 0.1% by weight of said antioxidant preservative agent.

16. The method of claim 15, wherein said carrier means is defined as an absorbent material, whereby said solution is impregnated therein.

17. The method of claim 15, wherein said absorbent material comprises an absorbent pad having a matrix for retaining the selectively impregnated solution to allow a rate of escape of a sufficiency of the vapors from said solution to exert the cockroach-repellent effectively throughout the desired area in which said absorbent pad is located.

18. The method of claim 17, including the step of enclosing said absorbent pad within a sealed container prior to placing said absorbent pad within said structure and wherein said sealed container is defined as an envelope that is impermeable to oxygen, air pollution, and light.

19. The method of claim 18, including the step of opening said envelope to expose said absorbent pad before placing said absorbent pad within said structure.

20. The method of claim 19, wherein said antioxidant preservative agent consists of nordihydroguaiaretic acid (NDGA).

21. The method of claim 20, wherein said linoleic acid consists of (Z,Z)-9, 12-octadienoic acid.

22. The method of claim 19, wherein said antioxidant preservative agent is selected from the group consisting of 2,6-di-tert-butyl-4-methylphenol (BHT), phytic acid, gallates, gallate derivative, 6-hydroxy-2,5,7,8-tetramethylchroman-2-carboxylic acid and natural or synthetic tocopherols.

23. The method of claim 19, wherein said antioxidant preservative agent is selected from the group consisting of oligomeric and polymeric non-alkaline lipophilic antioxidants.

24. The method of claim 19, wherein said matrix of said pad comprises an absorbent fabric material.

25. The method of claim 19, wherein said matrix of said pad comprises a permeable plastic material.

26. The method of claim 19, wherein said matrix of said pad comprises a porous ceramic material.

27. The method of claim 18, wherein said envelope is formed from a group of selective materials consisting of metal foils, films and continuous layers of condensation polymers.

28. The method of claim 18, wherein said envelope is formed from a group of selective materials consisting of metal foils, films and continuous layers of addition polymers.

* * * * *